("(12) United States Patent" "Moffitt")

(10) Patent No.: US 9,974,961 B2
(45) Date of Patent: *May 22, 2018

(54) COUPLED MONOPOLAR AND MULTIPOLAR PULSING FOR CONDITIONING AND STIMULATION

(71) Applicant: Boston Scientific Neuromodulation Corporation, Valencia, CA (US)

(72) Inventor: Michael A. Moffitt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/202,322

(22) Filed: Jul. 5, 2016

(65) Prior Publication Data

US 2016/0339253 A1    Nov. 24, 2016

Related U.S. Application Data

(63) Continuation of application No. 14/083,291, filed on Nov. 18, 2013, now Pat. No. 9,387,326, which is a continuation of application No. 11/752,898, filed on May 23, 2007, now Pat. No. 8,612,019.

(51) Int. Cl.
*A61N 1/36* (2006.01)
*A61N 1/05* (2006.01)

(52) U.S. Cl.
CPC ....... *A61N 1/36146* (2013.01); *A61N 1/0553* (2013.01); *A61N 1/36017* (2013.01); *A61N 1/36071* (2013.01); *A61N 1/36167* (2013.01)

(58) Field of Classification Search
None
See application file for complete search history.

(56) References Cited

U.S. PATENT DOCUMENTS

| | | |
|---|---|---|
| 5,097,833 A | 3/1992 | Campos |
| 5,117,826 A | 6/1992 | Bartelt et al. |
| 5,755,742 A | 5/1998 | Schuelke et al. |
| 6,292,701 B1 | 9/2001 | Prass et al. |
| 6,421,566 B1 | 7/2002 | Holsheimer |
| 6,516,227 B1 | 2/2003 | Meadows et al. |
| 6,546,288 B1 | 4/2003 | Levine |

(Continued)

OTHER PUBLICATIONS

Grill, W, et al., "Inversion of the Current-Distance Relationship by Transient Depolarization", IEEE Transactions of Biomedical Engineering vol. 44, No. 1, (Jan. 1997), 1-9.

(Continued)

*Primary Examiner* — Erica Lee
(74) *Attorney, Agent, or Firm* — Schwegman Lundberg & Woessner, P.A.

(57) ABSTRACT

A method and neurostimulation system of providing therapy to a patient is provided. A plurality of electrodes are placed in contact with tissue of a patient, a conditioning pulse is conveyed from the plurality of electrodes in one of a monopolar manner and a multipolar manner, and a stimulation pulse is conveyed from the plurality of electrodes in a different one of the monopolar manner and the multipolar manner. As one example, the sub-threshold conditioning pulse may be a depolarizing pulse conveyed from the plurality of electrodes to render a first region of the tissue less excitable to stimulation, and the stimulation pulse may be conveyed from the plurality of electrodes to stimulate a second different region of the tissue.

20 Claims, 10 Drawing Sheets

(56) References Cited

U.S. PATENT DOCUMENTS

| | | |
|---|---|---|
| 6,560,490 B2 | 5/2003 | Grill et al. |
| 6,609,031 B1 | 8/2003 | Law et al. |
| 6,675,046 B2 | 1/2004 | Holsheimer |
| 6,850,802 B2 | 2/2005 | Holsheimer |
| 6,892,097 B2 | 5/2005 | Holsheimer |
| 6,895,280 B2 | 5/2005 | Meadows et al. |
| 6,944,501 B1 | 9/2005 | Pless |
| 6,993,384 B2 | 1/2006 | Bradley et al. |
| 7,539,538 B2 | 5/2009 | Parramon et al. |
| 8,612,019 B2 | 12/2013 | Moffitt |
| 9,387,326 B2 | 7/2016 | Moffitt |
| 2002/0055779 A1 | 5/2002 | Andrews |
| 2002/0123780 A1 | 9/2002 | Grill et al. |
| 2003/0139781 A1 | 7/2003 | Bradley et al. |
| 2003/0204219 A1 | 10/2003 | Gielen |
| 2003/0204228 A1 | 10/2003 | Cross, Jr. et al. |
| 2004/0127953 A1 | 7/2004 | Kilgore et al. |
| 2005/0267546 A1 | 12/2005 | Parramon et al. |
| 2006/0122660 A1 | 6/2006 | Boveja et al. |
| 2007/0038250 A1 | 2/2007 | He et al. |
| 2008/0294211 A1 | 11/2008 | Moffitt |
| 2014/0074189 A1 | 3/2014 | Moffitt |

OTHER PUBLICATIONS

Hennings, K, et al., "Selective Activation of Small-Diameter Motor Fibres Using Exponentially Rising Waveforms: a theoretical study", Medical & Biological Engineering & Computing, vol. 43, (2005), 493-500.

Holsheimer, J, et al., "Effects of Electrode Geometry and Combination on Nerve Fibre Selectivity in Spinal Cord Stimulation", Med. & Bioi. Eng. & Comput, (1995), 676-682.

McIntyre, Cameron C, et al., "Selective microstimulation of central nervous system neurons", Annals of biomedical engineering., 28(3), (Mar. 2000), 219-233.

Poletto, C J, et al., "Elevating Pain Threshold in Humans Using Depolarizing Prepulses", IEEE Transactions on Biomedical Engineering vol. 49, No. 10, (Oct. 2002), 1221-1224.

"U.S. Appl. No. 11/752,898, 312 Amendment filed Oct. 25, 2013", 3 pgs.

"U.S. Appl. No. 11/752,898, Advisory Action dated Jun. 1, 2010", 4 pgs.

"U.S. Appl. No. 11/752,898, Appeal Brief filed Aug. 20, 2010", 13 pgs.

"U.S. Appl. No. 11/752,898, Decision on Pre-Appeal Brief Request dated Jun. 24, 2013", 7 pgs.

"U.S. Appl. No. 11/752,898, Examiner's Answer dated Oct. 27, 2010", 11 pgs.

"U.S. Appl. No. 11/752,898, Final Office Action dated Apr. 22, 2010", 6 pgs.

"U.S. Appl. No. 11/752,898, Non Final Office Action dated Nov. 25, 2009", 13 pgs.

"U.S. Appl. No. 11/752,898, Notice of Allowance dated Sep. 11, 2013", 9 pgs.

"U.S. Appl. No. 11/752,898, Reply Brief filed Dec. 3, 2010", 5 pgs.

"U.S. Appl. No. 11/752,898, Response filed Jan. 27, 2010 to Non Final Office Action dated Nov. 25, 2009", 10 pgs.

"U.S. Appl. No. 11/752,898, Response filed May 20, 2010 to Final Office Action dated Apr. 22, 2010", 9 pgs.

"U.S. Appl. No. 14/083,291, Advisory Action dated Mar. 19, 2015", 2 pgs.

"U.S. Appl. No. 14/083,291, Final Office Action dated Dec. 31, 2014", 8 pgs.

"U.S. Appl. No. 14/083,291, Non Final Office Action dated Jul. 31, 2014", 7 pgs.

"U.S. Appl. No. 14/083,291, Non Final Office Action dated Aug. 12, 2015", 8 pgs.

"U.S. Appl. No. 14/083,291, Notice of Allowance dated Mar. 11, 2016", 6 pgs.

"U.S. Appl. No. 14/083,291, Response filed Feb. 23, 2015 to Final Office Action dated Dec. 31, 2014", 7 pgs.

"U.S. Appl. No. 14/083,291, Response filed Sep. 17, 2014 to Non Final Office Action dated Jul. 31, 2014", 6 pgs.

"U.S. Appl. No. 14/083,291, Response filed Dec. 14, 2015 to Non Final Office Action dated Aug. 12, 2015", 7 pgs.

"Deep-brain stimulation of the subthalamic nucleus or the pars interna of the globus pallidus in Parkinson's disease", N. Engl J Med., 345(13), Author: Deep-Brain Stimulation for Parkinson's Disease Study Group, (Sep. 27, 2001), 956-963.

"International Application Serial No. PCT/US2008/006125, International Preliminary Report on Patentability dated Jun. 12, 2008", 9 pgs.

"International Application Serial No. PCT/US2008/006125, International Search Report dated Sep. 25, 2008", 4 pgs.

"International Application Serial No. PCT/US2008/006125, Written Opinion dated Sep. 25, 2008", 7 pgs.

Blumental, T D, et al., "Prepulses Reduce the Pain of Cutaneous Electrical Shocks", Psychosomatic Medicine, 63, (2000), 275-281.

Gorman, Peter H, et al., "The effect of Stimulus Parameters on the Recruitment Characteristics of Direct Nerve Stimulation", IEEE-TBME, vol. BME-30, No. 7, (Jul. 1983), 407-414.

COUPLED MONOPOLAR AND MULTIPOLAR PULSING FOR CONDITIONING AND STIMULATION

RELATED APPLICATION DATA

This application is a continuation of U.S. patent Ser. No. 14/083,291, filed Nov. 18, 2013, now issued as U.S. Pat. No. 9,387,326, which is a continuation of U.S. patent Ser. No. 11/752,898, filed May 23, 2007, now issued as U.S. Pat. No. 8,612,019, both of which application are herein incorporated by reference in their entirety.

FIELD OF THE INVENTION

The present invention relates to tissue stimulation systems, and more particularly, to a system and method for conditioning and stimulating nerve tissue.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

Each of these implantable neurostimulation systems typically includes one or more electrode carrying stimulation leads, which are implanted at the desired stimulation site, and a neurostimulator implanted remotely from the stimulation site, but coupled either directly to the stimulation lead(s) or indirectly to the stimulation lead(s) via a lead extension. Thus, electrical pulses can be delivered from the neurostimulator to the stimulation lead(s) to stimulate or activate a volume of neural tissue in accordance with a set of stimulation parameters and provide the desired efficacious therapy to the patient. A typical stimulation parameter set may include the electrodes that are sourcing (anodes) or returning (cathodes) the stimulation pulses at any given time, as well as the magnitude, duration, and rate of the stimulation pulses. The neurostimulation system may comprise a handheld patient programmer to remotely instruct the neurostimulator to generate electrical stimulation pulses in accordance with selected stimulation parameters. The handheld programmer may, itself, be programmed by a technician attending the patient, for example, by using a Clinician's Programmer Station (CPS), which typically includes a general purpose computer, such as a laptop, with a programming software package installed thereon.

The best stimulus parameter set will typically be one that provides stimulation energy to the volume of neural tissue that must be stimulated in order to provide the therapeutic benefit (e.g., pain relief), while minimizing the volume of non-target neural tissue that is stimulated. However, because the target neural tissue (i.e., the tissue associated with the therapeutic effects) and non-target neural tissue (i.e., the tissue associated with undesirable side effects) are often juxtaposed, therapeutically stimulating neural tissue while preventing side effects may be difficult to achieve.

For example, in SCS, stimulation of the spinal cord creates the sensation known as paresthesia, which can be characterized as an alternative sensation that replaces the pain signals sensed by the patient. To produce the feeling of paresthesia without inducing involuntary motor movements within the patient, it is often desirable to preferentially stimulate nerve fibers in the dorsal column (DC nerve fibers), which primarily include sensory nerve fibers, over nerve fibers in the dorsal roots (DR nerve fibers), which include both sensory nerve fibers and motor reflex nerve fibers. While DC nerve fibers are the intended targets in conventional SCS, in fact, the DR nerve fibers often are recruited first because of geometric, anatomical, and physiological reasons. For example, the DR nerve fibers have larger diameters than the largest nearby DC nerve fibers, and thus, have a lower threshold at which they are excited. Other factors that contribute to the lower threshold needed to excite DR nerve fibers are the different orientations of the DC nerve fibers and DR nerve fibers, the curved shape of the DR nerve fibers, and the inhomogeneity and anisotropy of the surrounding medium at the entrance of the DR nerve fibers into the spinal cord. Thus, DR nerve fibers may still generate action potentials at lower voltages than will nearby DC nerve fibers. As a result, the DC nerve fibers that are desired to be stimulated have a lower probability to be stimulated than do the DR nerve fibers, and thus, the reflex motor nerve fibers intermingled among the sensor nerve fibers of a dorsal root are often recruited, leading to discomfort or muscle twitching, thereby preventing satisfactory paresthesia coverage.

For reasons such as this, it is often desirable to modify the threshold at which neural tissue is activated in a manner that maximizes excitation of the target neural tissue, while minimizing excitation of the non-target neural tissue. This can be accomplished by applying depolarizing sub-threshold conditioning pulses (or pre-pulses) to render neural tissue (and in this case, the non-target neural tissue) less excitable to the subsequent stimulation pulse and/or applying hyperpolarizing sub-threshold conditioning pulses to render tissue (and in this case, target neural tissue) more excitable to the subsequent stimulation pulse.

Pre-pulsing was designed in the context of monopolar stimulation; that is, monopolar pre-pulses followed by monopolar stimulation pulses. Subsequent conditioning arrangements have contemplated the use of multipolar pre-pulses followed by multipolar stimulation pulses for SCS and DBS applications. For example, as shown in FIG. 1, it is known to place three electrodes 1a-1c in contact with a spinal cord SC along a line that is transverse to the axis of the spinal cord SC, so that the center electrode 1b is located at the center of the DC nerve fibers, and the two outer electrodes 1a, 1c are located adjacent the DR nerve fibers extending from the spinal cord SC.

Tripolar conditioning energy, and then tripolar stimulation energy, is conveyed from the electrodes 1a-1c in accordance with a pulse pattern that preferentially stimulates the DC nerve fibers, while inhibiting the stimulation of the DR nerve fibers. In particular, as shown in FIG. 2, during a conditioning period, depolarizing, sub-threshold, cathodic pre-pulses 2 are respectively conveyed from the outer electrodes 1a, 1c to render the DR nerve fibers less excitable, while a hyperpolarizing, sub-threshold, anodic pre-pulse 4 is conveyed from the center electrode 1b to render the DC nerve fibers more excitable. During a stimulation period, anodic pulses 6 are then conveyed from the outer electrodes 1a, 1c, and a cathodic stimulation pulse 8 is conveyed from the center electrode 1b. Because the DR nerve fibers have been rendered less excitable by the depolarized pre-pulses 2, the subsequent anodic pulses 6 will not stimulate the DR nerve fibers. In contrast, because the DC nerve fibers have been rendered more excitable by the hyperpolarizing pre-pulse 4, the subsequent cathodic stimulation pulse 8 will stimulate the DC nerve fibers.

While coupling monopolar conditioning pulses with monopolar stimulation pulses, and coupling multipolar conditioning pulses with multipolar stimulation pulses, has proven successful in preferentially stimulating nerve fibers, there are certain benefits to monopolar conditioning and stimulation over multipolar conditioning and stimulation, and vice versa. Thus, the benefits of coupling conditioning pulses and stimulation pulses may not be fully maximized.

There, thus, remains a need for an improved neurostimulation method and system that couples conditioning pulses with stimulation pulses.

SUMMARY OF THE INVENTION

In accordance with a first aspect of the present inventions, a method of providing therapy to a patient is provided. The method comprises placing a plurality of electrodes in contact with tissue of a patient. For example, the tissue may be spinal cord tissue, and the plurality of electrodes may be arranged transversely relative to the axis of the spinal cord. The method further comprises conveying at least one conditioning pulse from the plurality of electrodes in one of a monopolar manner and a multipolar manner, and conveying at least one stimulation pulse from the plurality of electrodes in a different one of the monopolar manner and the multipolar manner.

That is, the conditioning pulse(s) may be conveyed from the plurality of electrodes in a monopolar manner, in which case, the stimulation pulse(s) is conveyed from the plurality of electrodes in a multipolar manner, or the conditioning pulse(s) may be conveyed from the plurality of electrodes in a multipolar manner, in which case, the stimulation pulse(s) is conveyed from the plurality of electrodes in a monopolar manner. In one method, the conditioning pulse(s) may be conveyed from the plurality of electrodes before the stimulation pulse(s) is conveyed from the plurality of electrodes.

As one example, the conditioning pulse(s) may be a depolarizing pulse conveyed from the plurality of electrodes to render a first region of the tissue less excitable to stimulation, and the stimulation pulse(s) may be conveyed from the plurality of electrodes to stimulate a second different region of the tissue. In this example, the first region may comprise dorsal root (DR) nerve fibers, and the second region may comprise dorsal column (DC) nerve fibers. Or, the first region may comprise DC nerve fibers, and the second region may comprise DR nerve fibers. As another example, the conditioning pulse(s) may be a hyperpolarizing pulse conveyed from the plurality of electrodes to render a first region of the tissue (e.g., DC nerve fibers) more excitable to stimulation, and the stimulation pulse(s) may be conveyed from the plurality of electrodes to stimulate the first tissue region.

Although the present inventions should not be so limited in their broadest aspects, the conveyance of the conditioning pulse(s) and stimulation pulse(s) in these different manners, allows the benefits of both monopolar and multipolar electrode arrangements to be selectively utilized.

In accordance with a second aspect of the present inventions, a neurostimulation system is provided. The system comprises a plurality of electrical contacts, and output stimulation circuitry capable of outputting electrical pulses to the plurality of electrical contacts in accordance with a pulse pattern. The neurostimulation system further comprises control circuitry capable of defining the pulse pattern, such that the electrical pulses comprise at least one conditioning pulse(s) outputted to the plurality of electrical contacts in one of a monopolar and a multipolar manner, and at least one stimulation pulse(s) outputted to the plurality of electrical contacts in a different one of the monopolar and multipolar manner.

That is, the conditioning pulse(s) is outputted to the plurality of electrical contacts in a monopolar manner, in which case, the stimulation pulse(s) is outputted to the plurality of electrical contacts in a multipolar manner, or the conditioning pulse(s) is outputted to the plurality of electrical contacts in a multipolar manner, in which case, the stimulation pulse(s) is outputted to the plurality of electrodes in a monopolar manner. In one embodiment, the conditioning pulse is one of a cathodic pulse and an anodic pulse, and the simulation pulse is a different one of the cathodic pulse and the anodic pulse. In another embodiment, the conditioning pulse(s) is outputted to the plurality of electrical contacts before the stimulation pulse(s) is outputted to the plurality of electrical contacts.

In one embodiment, the neurostimulation system further comprises one or more stimulation leads carrying a plurality of electrodes in electrical communication with the plurality of electrical contacts. For example, in one embodiment, the one or more stimulation leads comprises one or more spinal cord stimulation leads. In this case, the spinal cord stimulation leads may comprise a paddle lead, and the plurality of electrodes may comprise at least three electrodes arranged along a line transverse to an axis of the paddle lead. The neurostimulation system may further comprise a memory capable of storing a set of stimulation parameters, in which case, the control circuitry is capable of defining the pattern in accordance with the stimulation parameter set. The neurostimulation system may further comprise a case, in which case, the plurality of electrical contacts, output stimulation circuitry, and control circuitry can be contained in the case to form a neurostimulator.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

At the outset, it is noted that the present invention may be used with an implantable pulse generator (IPG), radio frequency (RF) transmitter, or similar electrical stimulator, that may be used as a component of numerous different types of stimulation systems. The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, a peripheral nerve stimulator, or in any other neural stimulator configured to treat urinary incontinence, sleep apnea, shoulder subluxation, etc.

Figure 1:
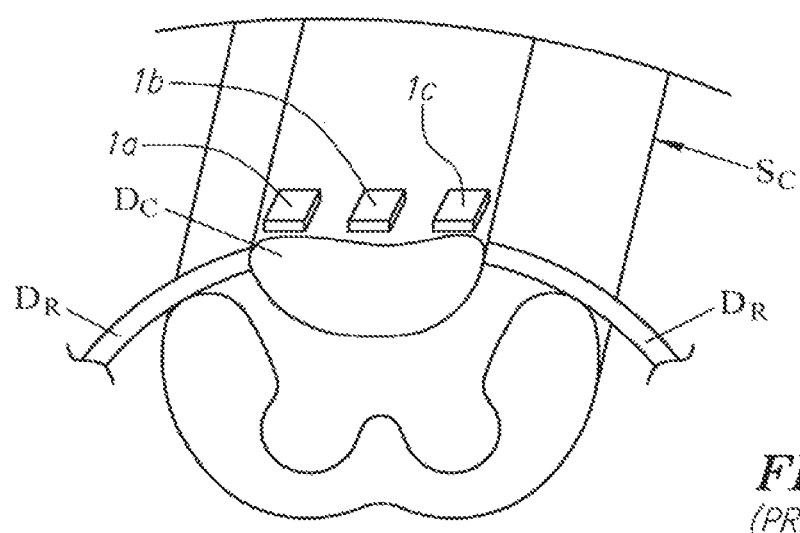
FIG. 1 is a perspective view of a prior art transverse electrode arrangement located on a spinal cord.
Figure 2:
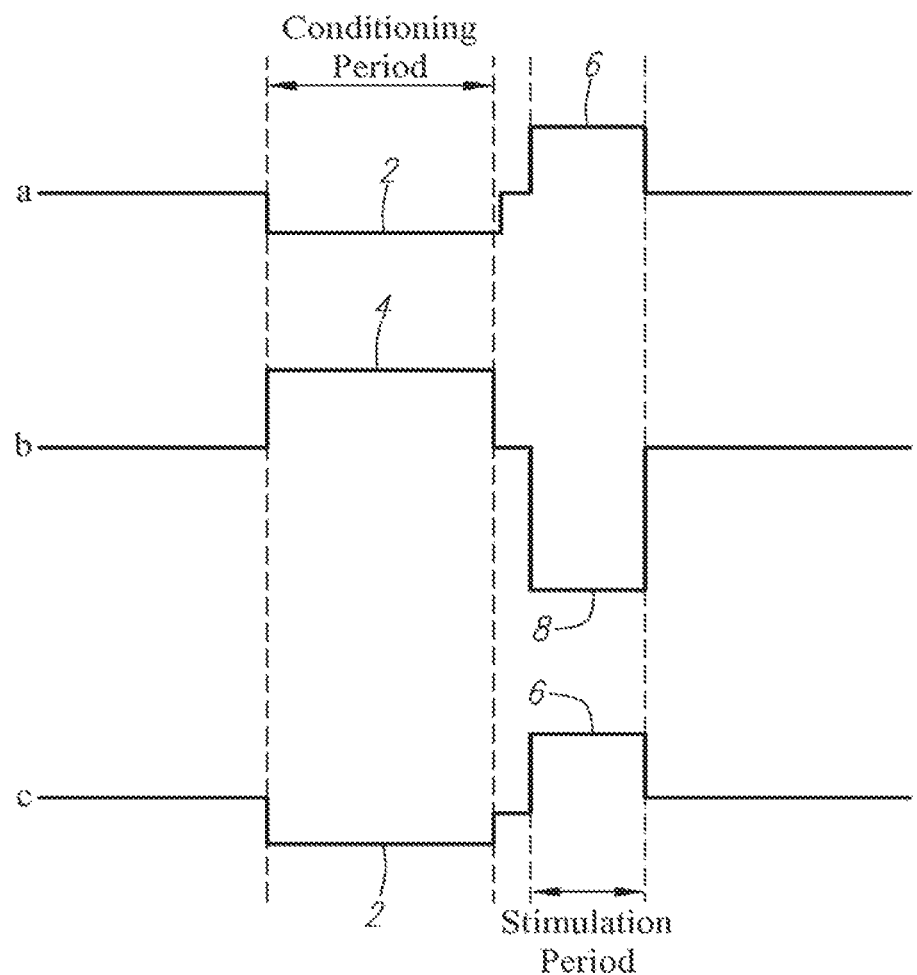
FIG. 2 is a prior art pulse timing diagram used to condition and stimulate the spinal cord with the electrode arrangement of FIG. 1.
Figure 3:
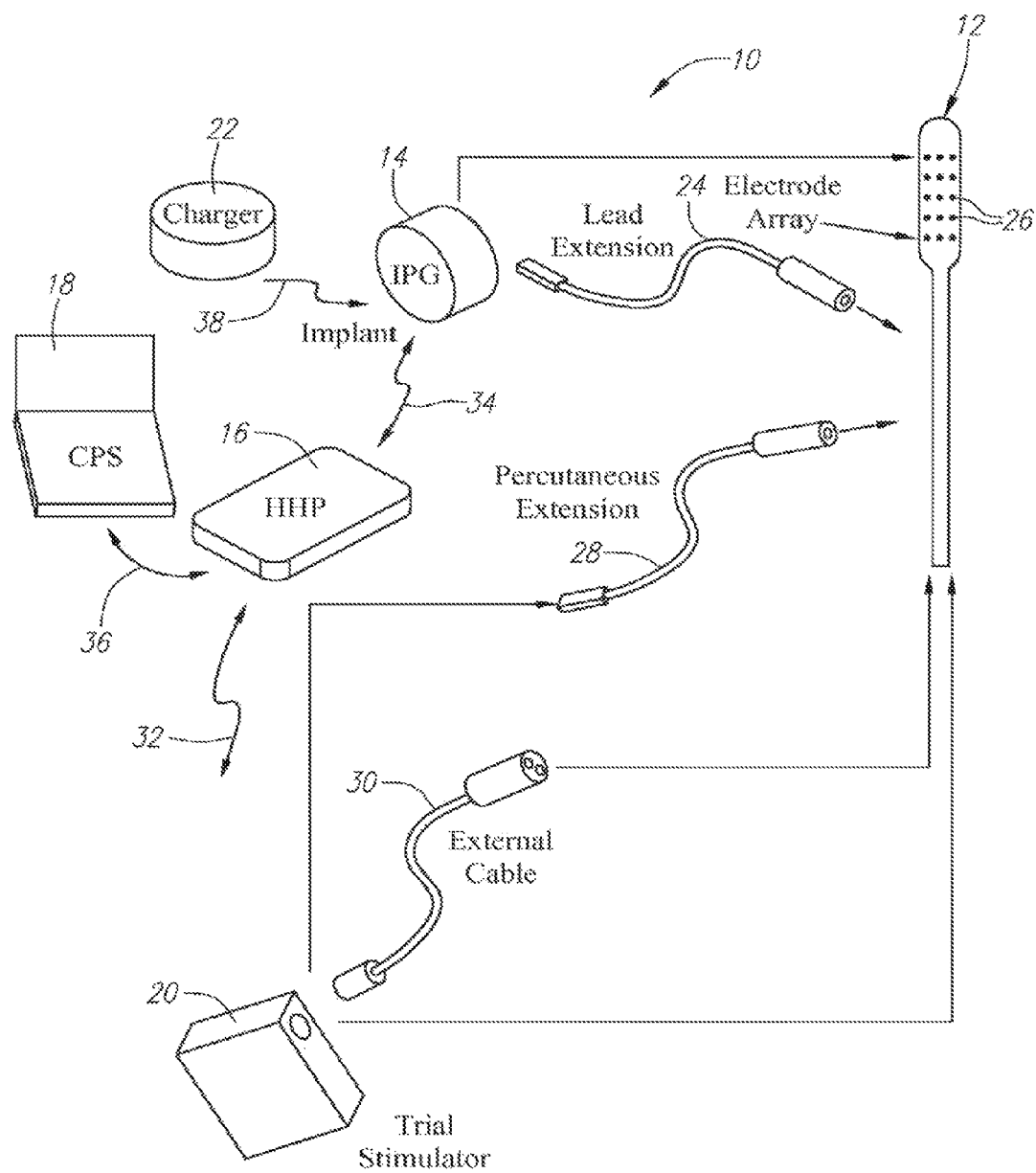
FIG. 3 is plan view of one embodiment of a spinal cord stimulation (SCS) system arranged in accordance with the present inventions.

Turning first to FIG. 3, an exemplary SCS system 10 generally at least one implantable stimulation lead 12, an implantable pulse generator (IPG) 14 (or alternatively RF receiver-stimulator), an external handheld programmer (HHP) 16, a Clinician's Programmer Station (CPS) 18, an External Trial Stimulator (ETS) 20, and an external charger 22.

The IPG 14 is physically connected via a percutaneous lead extension 24 to the stimulation lead 12, which carries an array of electrodes 26. The the ETS 20 may also be physically connected via the percutaneous lead extensions 28 and external cable 30 to the stimulation lead 12. The ETS 20, which has similar pulse generation circuitry as the IPG 14, also provides electrical stimulation energy to the electrode array 26 in accordance with a set of stimulation parameters. The major difference between the ETS 20 and the IPG 14 is that the ETS 20 is a non-implantable device that is used on a trial basis after the stimulation lead 12 has been implanted and prior to implantation of the IPG 14, to test the effectiveness of the stimulation that is to be provided.

The HHP 16 may be used to telemetrically control the ETS 20 via a bi-directional RF communications link 32. Once the IPG 14 and stimulation lead 12 is implanted, the HHP 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the HHP 16 being present.

The CPS 18 provides clinician detailed stimulation parameters for programming the IPG 14 and ETS 20 in the operating room and in follow-up sessions. The CPS 18 may perform this function by indirectly communicating with the IPG 14 or ETS 20, through the HHP 16, via an IR communications link 36. Alternatively, the CPS 18 may directly communicate with the IPG 14 or ETS 20 via an RF communications link (not shown). The external charger 22 is a portable device used to transcutaneously charge the IPG 14 via an inductive link 38.

For purposes of brevity, the details of the HHP 16, CPS 18, ETS 20, and external charger 22 will not be described herein. Details of exemplary embodiments of these devices are disclosed in U.S. Pat. No. 6,895,280, which is expressly incorporated herein by reference.

Figure 4:
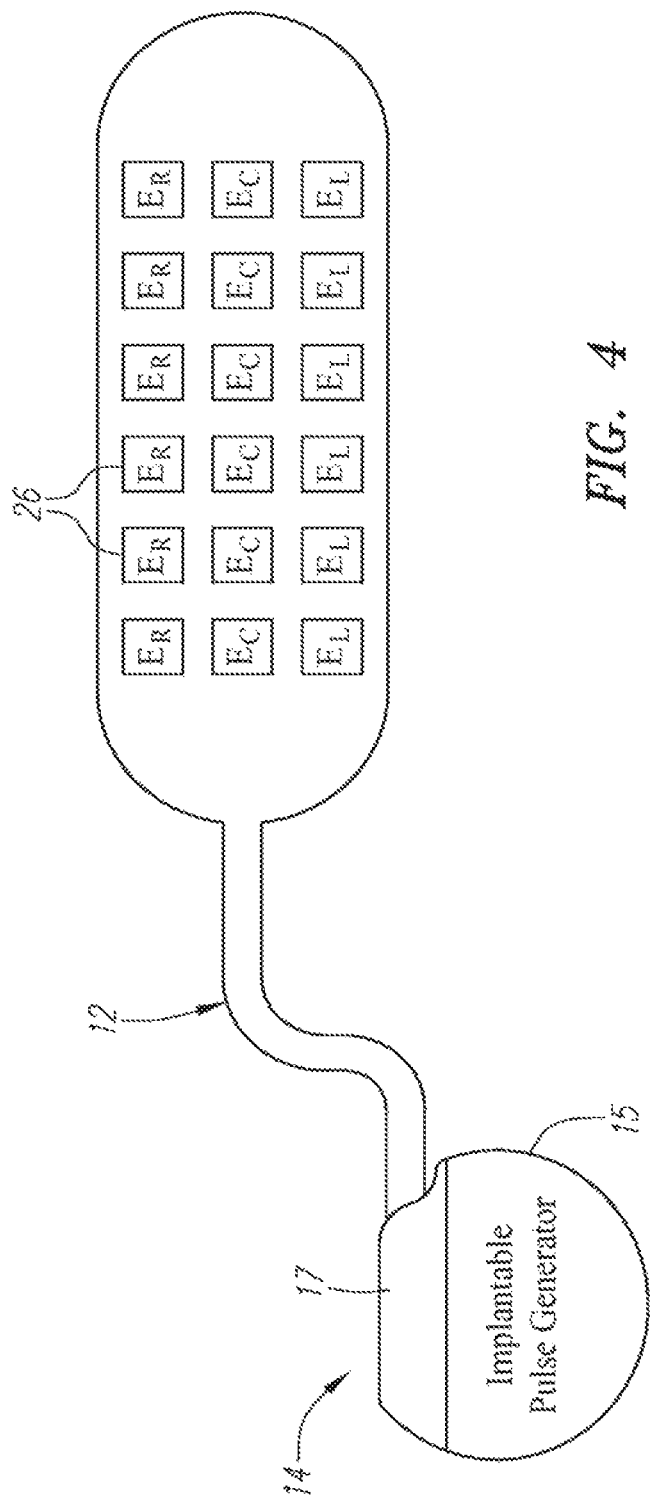
FIG. 4 is a plan view of an implantable pulse generator (IPG) and stimulation lead used in the SCS system of FIG. 3.

Referring further to FIG. 4, the IPG 14 comprises an outer case 15 for housing the electronic and other components (described in further detail below), and a connector 17 in which the proximal end of the stimulation lead 12 mates in a manner that electrically couples the electrodes 26 to the electronics within the outer case 15. The outer case 15 is composed of an electrically conductive, biocompatible material, such as titanium, and forms a hermetically sealed compartment wherein the internal electronics are protected from the body tissue and fluids. In some cases, the outer case 15 serves as an electrode.

In the illustrated embodiment, the stimulation lead 12 is a paddle lead having a flat paddle-shaped distal end, wherein the electrodes 26 are carried on one side of the paddle. The electrodes 26 are arranged in three columns along the axis of the stimulation lead 12, with the electrodes in one lateral column (left column when lead 12 is introduced into the patient in the rostral direction) being labeled $E_L$, the electrodes in the center column being labeled Ec, and the electrodes in the other lateral column (right column when lead 12 is introduced into the patient in the rostral direction) being labeled $E_R$. Each row of the electrodes 26 (which includes a left electrode $E_L$, a center electrode $E_C$, and a right electrode $E_R$) is arranged in a line transversely to the axis of the lead 12. The actual number of leads and electrodes will, of course, vary according to the intended application. In alternative embodiments, one or more percutaneous leads with electrodes arranged in-line along the leads can be provided.

As will be described in further detail below, the IPG 14 includes pulse generation circuitry that provides electrical conditioning and stimulation energy to the electrode array 26 in accordance with a set of parameters. Such parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and delay between conditioning pre-pulses and stimulation pulses (measured in microseconds). Significantly, as will be described in further detail below, the electrical energy provided by the IPG 14 or ETS 20 generates conditioning pulses in a monopolar manner and generates stimulation pulses in a multipolar manner, and/or generates conditioning pulses in a multipolar manner and generates stimulation pulses in a monopolar manner.

With respect to the pulse patterns provided during operation of the SCS system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case, so that the electrical current has a path from the energy source contained within the IPG case to the tissue and a return path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 26 is activated along with the case of the IPG 14, so that electrical energy is transmitted between the selected electrode 26 and case. Monopolar delivery may also occur when one or more of the lead electrodes 26 are activated along with a large group of lead electrodes 26 located remotely from the one more lead electrodes 26 so as to create a monopolar effect; that is, electrical energy is conveyed from the one or more lead electrodes 26 in a relatively isotropic manner.

Bipolar delivery occurs when two of the lead electrodes 26 are activated as anode and cathode, so that electrical energy is transmitted between the selected electrodes 26. For example, the center electrode $E_C$ may be activated as an anode at the same time that the left electrode $E_L$ is activated as a cathode. Tripolar delivery occurs when three of the lead electrodes 26 are activated, two as anodes and the remaining one as a cathode, or two as cathodes and the remaining one as an anode. For example, the left and right electrodes $E_L$, $E_R$ may be activated as anodes at the same time that the center electrode $E_C$ is activated as a cathode.

Figure 5:
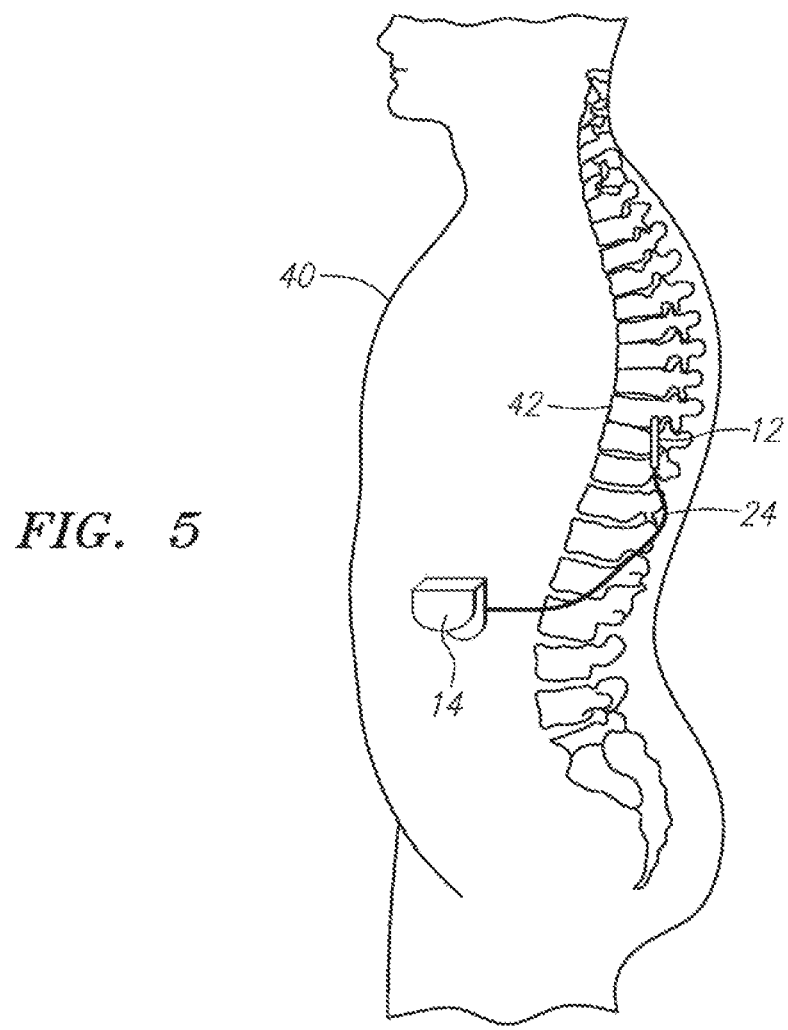
FIG. 5 is a plan view of the SCS system of FIG. 3 in use with a patient.

Referring to FIG. 5, the stimulation lead 12 is implanted within the spinal column 42 of a patient 40. The preferred placement of the stimulation lead 12 is adjacent, i.e., resting upon, the spinal cord area to be stimulated. Due to the lack of space near the location where the stimulation lead 12 exit the spinal column 40, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the stimulation lead 12. After implantation, the IPG 14 is used to provide the therapeutic stimulation under control of the patient.

Figure 6:
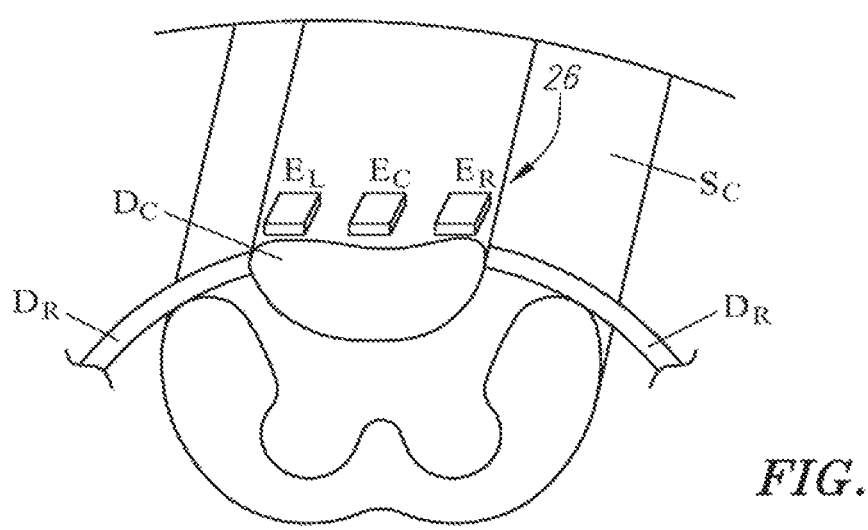
FIG. 6 is a perspective view of one row of electrodes of the stimulation lead of FIG. 4 is contact with a spinal cord.

As shown in FIG. 6, a row of electrodes 26 are arranged along a line transverse to the axis of the spinal cord SC, such that the center electrode $E_C$ is located over the center of the dorsal column (DC) nerve fibers, and the left and right electrodes $E_L$, $E_R$ are laterally placed from the center of the DC nerve fibers adjacent the respective dorsal root (DR) nerve fibers, thereby forming a medio-lateral electrode configuration. Alternatively, if a percutaneous stimulation lead is used, the electrodes of the lead can be arranged in a line along the axis of the spinal cord SC, or if multiple percutaneous stimulation leads are used, the electrodes may be arranged in unstaggered columns, such that a row of electrodes may be placed in contact with the spinal cord SC in the manner shown in FIG. 6. In a case where only two columns of electrodes are provided, one column of electrodes can be placed laterally on one side of the centerline of the spinal cord SC and the other column of electrodes can be placed laterally on the other side of the centerline of the spinal cord SC. In alternative embodiments, electrodes may be rostro-caudally arranged in a line parallel to the axis of the spinal cord SC.

Figure 7:
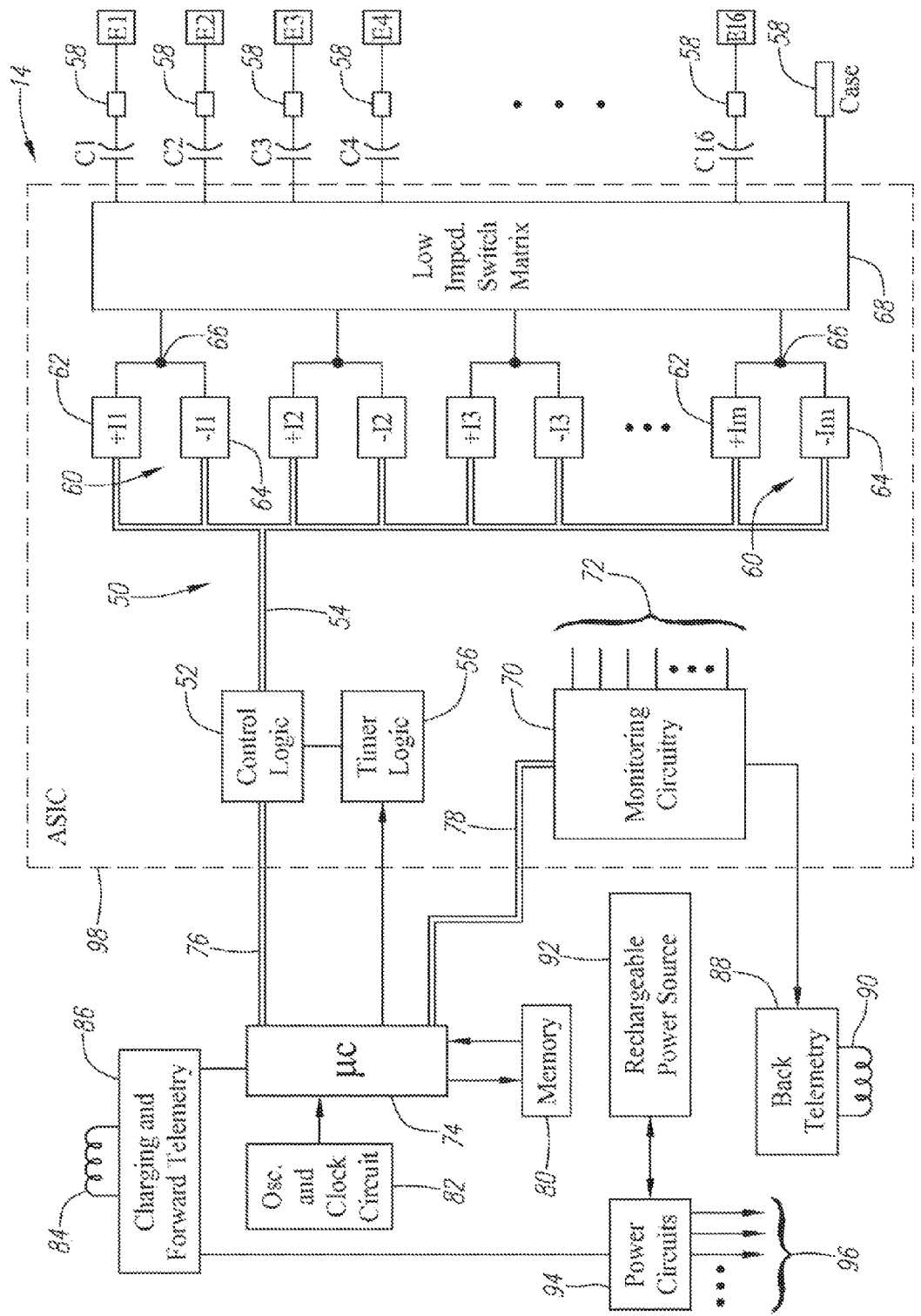
FIG. 7 is a block diagram of the internal components of the IPG of FIG. 4.

Turning next to FIG. 7, the main internal components of the IPG 14 will now be described. The IPG 14 includes analog output circuitry 50 capable of individually generating electrical pulses of specified amplitude under control of control logic 52 over data bus 54. The pulse rate and pulse width of the electrical pulses output by the IPG 14 are controlled using the timer logic circuitry 56. The timer logic circuitry 56 may have a suitable resolution, e.g., 10 μs. These electrical pulses are supplied via capacitors C1-Cn to electrical contacts 58 corresponding to electrodes E1-En and the case electrode. As will be described in further detail below, the analog output circuitry 50 is capable of outputting both sub-threshold conditioning pulses and stimulation pulses to the electrical contacts 58, and thus, the electrodes E1-En.

In the illustrated embodiment, the analog output circuitry 50 comprises a plurality m independent current source pairs 60 capable of supplying electrical energy to the electrical contacts 58 at a specified and known amperage. One current source 62 of each pair 60 functions as a positive (+) or anodic current source, while the other current source 64 of each pair 60 functions as a negative (−) or cathodic current source. The outputs of the anodic current source 62 and the cathodic current source 64 of each pair 60 are connected to a common node 66. The analog output circuitry 50 further comprises a low impedance switching matrix 68 through which the common node 66 of each current source pair 60 is connected to any of the electrical contacts 58 via the capacitors C1-Cn. Alternatively, the analog output circuitry 50 does not use a low impedance switching matrix 68, but rather uses a bi-directional current source for each of the electrical contacts 58.

Thus, for example, it is possible to program the first anodic current source 62 (+I1) to produce a pulse of +4 ma (at a specified rate and for a specified duration), and to synchronously program the second cathodic current source 64 (−I2) to similarly produce a pulse of −4 ma (at the same rate and pulse width), and then connect the node 66 of the anodic current source 62 (+I1) to the electrical contact 58 corresponding to electrode E3, and connect the node 80 of the cathodic current source 64 (−I2) to the electrical contact 58 corresponding to electrode E1.

Hence, it is seen that each of the programmable electrical contacts 58 can be programmed to have a positive (sourcing current), a negative (sinking current), or off (no current) polarity. Further, the amplitude of the current pulse being sourced or sunk from a given electrical contact 58 may be programmed to one of several discrete levels. In one embodiment, the current through each electrical contact 58 can be individually set from 0 to ±10 ma in steps of 100 µa, within the output voltage/current requirements of the IPG 14. Additionally, in one embodiment, the total current output by a group of electrical contacts 58 can be up to ±20 ma (distributed among the electrodes included in the group). Moreover, it is seen that each of the electrical contacts 58 can operate in a multipolar mode, e.g., where two or more electrical contacts are grouped to source/sink current at the same time. Alternatively, each of the electrical contacts 58 can operate in a monopolar mode where, e.g., the electrical contacts 58 are configured as cathodes (negative), and case of the IPG 14 is configured as an anode (positive).

It can be appreciated that an electrical contact 58 may be assigned an amplitude and included with any of up to k possible groups, where k is an integer corresponding to the number of channels, and in preferred embodiment is equal to 4, and with each channel k having a defined pulse width and pulse rate. Other channels may be realized in a similar manner. Thus, each channel identifies which electrical contacts 58 (and thus electrodes) are selected to synchronously source or sink current, the pulse amplitude at each of these electrical contacts, and the pulse width and pulse rate.

In an alternative embodiment, rather than using independent controlled current sources, independently controlled voltage sources for providing electrical pulses of a specified and known voltage at the electrical contacts 58 can be provided. The operation of this output circuitry, including alternative embodiments of suitable output circuitry for performing the same function of generating electrical pulses of a prescribed amplitude and width, is described more fully in U.S. Pat. Nos. 6,516,227 and 6,993,384, which are expressly incorporated herein by reference.

The IPG 14 further comprises monitoring circuitry 70 for monitoring the status of various nodes or other points 72 throughout the IPG 14, e.g., power supply voltages, temperature, battery voltage, and the like. The IPG 14 further comprises processing circuitry in the form of a microcontroller 74 that controls the control logic 52 over data bus 76, and obtains status data from the monitoring circuitry 70 via data bus 78. The IPG 14 additionally controls the timer logic 56. The IPG 14 further comprises memory 80 and oscillator and clock circuit 82 coupled to the microcontroller 74. The microcontroller 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the microcontroller 74 generates the necessary control and status signals, which allow the microcontroller 74 to control the operation of the IPG 14 in accordance with a selected operating program and parameters. In controlling the operation of the IPG 14, the microcontroller 74 is able to individually generate electrical pulses at the electrodes 26 using the analog output circuitry 50, in combination with the control logic 52 and timer logic 56, thereby allowing each electrode 26 to be paired or grouped with other electrodes 26, including the monopolar case electrode, and to control the polarity, amplitude, rate, pulse width, and channel through which the current stimulus pulses are provided.

The IPG 14 further comprises an alternating current (AC) receiving coil 84 for receiving programming data (e.g., the operating program and/or stimulation parameters) from the HHP 16 in an appropriate modulated carrier signal, and charging and forward telemetry circuitry 86 for demodulating the carrier signal it receives through the AC receiving coil 84 to recover the programming data, which programming data is then stored within the memory 80, or within other memory elements (not shown) distributed throughout the IPG 14.

The IPG 14 further comprises back telemetry circuitry 88 and an alternating current (AC) transmission coil 90 for sending informational data sensed through the monitoring circuitry 70 to the HHP 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the HHP 16, all programmable settings stored within the IPG 14 may be uploaded to the HHP 16.

The IPG 14 further comprises a rechargeable power source 92 and power circuits 94 for providing the operating power to the IPG 14. The rechargeable power source 92 may, e.g., comprise a lithium-ion or lithium-ion polymer battery. The rechargeable battery 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits, also known as "inverter circuits") received by the AC receiving coil 84. To recharge the power source 92, an external charger (not shown), which generates the AC magnetic field, is placed against, or otherwise adjacent, to the patient's skin over the implanted IPG 14. The AC magnetic field emitted by the external charger induces AC currents in the AC receiving coil 84. The charging and forward telemetry circuitry 86 rectifies the AC current to produce DC current, which is used to charge the power source 92. While the AC receiving coil 84 is described as being used for both wirelessly receiving communications (e.g., programming and control data) and charging energy from the external device, it should be appreciated that the AC receiving coil 84 can be arranged as a dedicated charging coil, while another coil, such as coil 90, can be used for bi-directional telemetry.

As shown in FIG. 7, much of the circuitry included within the IPG 14 may be realized on a single application specific integrated circuit (ASIC) 98. This allows the overall size of the IPG 14 to be quite small, and readily housed within a suitable hermetically-sealed case. Alternatively, most of the circuitry included within the IPG 14 may be located on multiple digital and analog dies, as described in U.S. patent application Ser. No. 11/177,503, filed Jul. 8, 2005, which is incorporated herein by reference in its entirety. For example, a processor chip, such as an application specific integrated circuit (ASIC), can be provided to perform the processing functions with on-board software. An analog IC (AIC) can be provided to perform several tasks necessary for the functionality of the IPG 14, including providing power regulation, stimulus output, impedance measurement and monitoring. A digital IC (DigIC) may be provided to function as the primary interface between the processor IC and analog IC by controlling and changing the levels and sequences of the current output by the stimulation circuitry in the analog IC when prompted by the processor IC.

It should be noted that the diagram of FIG. 7 is functional only, and is not intended to be limiting. Those of skill in the art, given the descriptions presented herein, should be able to readily fashion numerous types of IPG circuits, or equivalent circuits, that carry out the functions indicated and described. Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCS system 10 may alternatively utilize an implantable receiver-stimulator (not shown) connected to the stimulation lead 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Significantly, the IPG 14 (or ETS 20) utilizes the inherent differences between monopolar electrode arrangements and multipolar electrode arrangements to preferentially stimulate a tissue region relative to another tissue region, and in the illustrated case, to preferentially stimulate the DC nerve fibers, while suppressing stimulation of the DR nerve fibers, or alternatively, to preferentially stimulate the DR nerve fibers, while suppressing stimulation of the DC nerve fibers.

Figure 8:
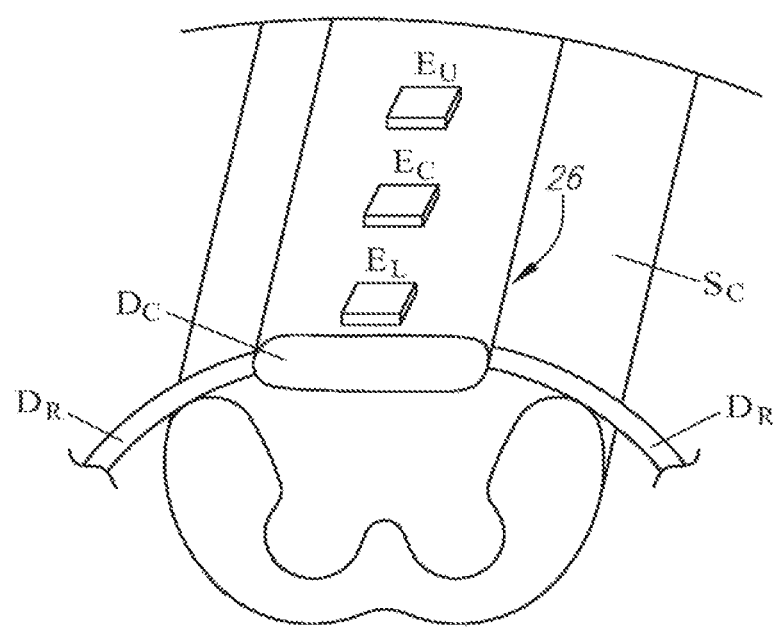
FIG. 8 is a perspective view of a prior art rostro-caudal electrode arrangement located on a spinal cord.
Figure 9A:
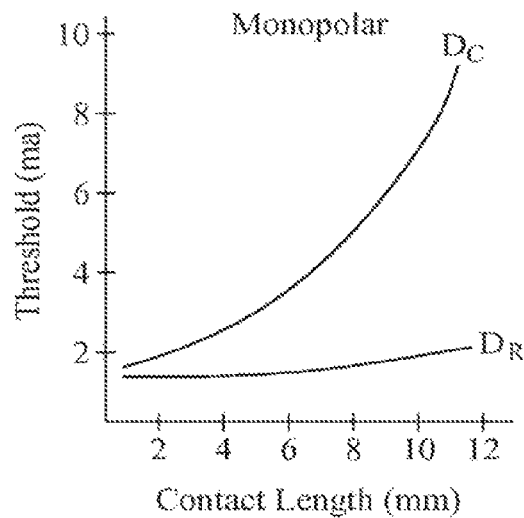
FIGS. 9a-9c are prior art threshold-electrode contact plots resulting from respectively applying monopolar, bipolar, and tripolar stimulation energy to the electrode arrangement of FIG. 8.
Figure 9B:
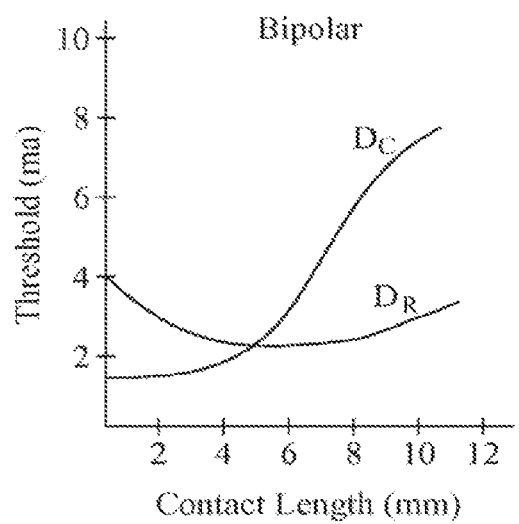
Figure 9C:
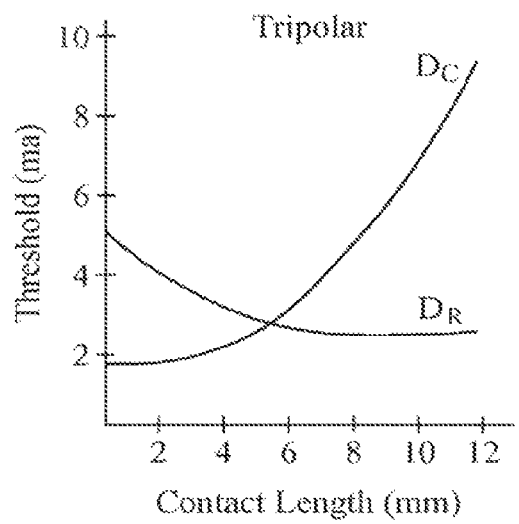

Notably, the stimulation thresholds of the respective DC nerve fibers and DR nerve fibers largely depend on whether electrical energy is applied to fibers in a monopolar manner or electrical energy is applied to the fibers in a multipolar manner. For example, based on modeled data of three electrodes (an upper (or rostral) electrode $E_U$, a center electrode $E_C$, and an lower (or caudal) electrode $E_L$) arranged along the axis of a spinal cord (rostro-caudally), as illustrated in FIG. 8, the threshold of DC nerve fibers and DR nerve fibers vastly vary both as a function of electrode contact length and as a function of the manner in which the electrical energy is delivered (i.e., monopolar bipolar, or tripolar), as shown in FIGS. 9a-9c. (See *Effects of Electrode Geometry and Combination on Nerve Fibre Selectivity in Spinal Cord Stimulation*, Holsheimer, et al., Medical & Biological Engineering & Computing, September 1995).

This model assumes that the DR nerve fibers enter the spinal cord at a rostro-caudal level corresponding to the center electrode $E_C$. The stimulation thresholds of the DC nerve fibers and DR nerve fibers are defined as the minimum electrical current between the cathode and anode(s) needed for their respective excitation when using a pulse duration of 210 μs. In monopolar stimulation, the center electrode $E_C$ was used as the cathode and the outer boundary of the model was used as the anode. In bipolar stimulation, the center electrode $E_C$ was used as the cathode and the lower electrode $E_U$ was used as the anode. In tripolar stimulation, the center electrode $E_C$ was used as the cathode and both the upper and lower electrodes $E_U$, $E_L$ were used as anodes. In bipolar and tripolar stimulation, all of the electrodes were assumed to have the same geometry.

As can be seen from FIG. 9a, when monopolar energy is applied, the stimulation current threshold is higher for DC nerve fibers than it is for DR nerve fibers for all electrode contact lengths, with the threshold disparity between DC and DR nerve fibers exponentially increasing as the electrode contact length (rostro-caudal dimension) increases. It is believed that the monopolar energy preferentially acts on DR nerve fibers over DC nerve fibers, because the largest DR nerve fibers are believed to be larger than the largest DC nerve fibers, the curvature of the DR nerve fibers renders them more sensitive to monopolar energy, and the DR nerve fibers traverse more inhomogeneities in their path as they move from the cerebral spinal fluid (CSF) into the spinal cord SC, making them more excitable.

As can be seen from FIGS. 9b and 9c, the stimulation current threshold is lower for DC nerve fibers than it is for DR nerve fibers for electrode contact lengths up to about 4 mm. It can be appreciated from this that, for a given range of electrode contact lengths, the stimulation current threshold for a DR nerve fiber will be less than the stimulation current threshold for a DC nerve fiber when electrical energy is applied to the spinal cord in a monopolar manner, and the stimulation current threshold for a DC nerve fiber will be less than the stimulation current threshold for a DR nerve fiber when electrical energy is applied to the spinal cord SC in a multipolar manner. Thus, to preferentially act on DR nerve fibers, electrical energy can be applied in a monopolar manner, and to preferentially act on DC nerve fibers, electrical energy can be applied in a multipolar manner.

In addition to providing selectivity between DC nerve fibers and DR nerve fibers, the differences in monopolar electrode arrangements and multipolar electrode arrangements affect the field decay of the applied electrical energy. In particular, the region of tissue affected by electrical energy when applied in a monopolar manner is greater than the region of tissue affected by electrical energy when applied in a bipolar manner, since a monopolar field decays approximately inversely to the distance to the electrode, whereas a bipolar field decays approximately inversely to the square of the distance to the electrode. While the effect of bipolar electrical energy does not extend as far as that of monopolar electrical energy, the thresholds for activation of fibers in the immediate vicinity of a bipolar electrode is generally lower than the thresholds for activation of fibers in the immediate vicinity of a monopolar electrode. Thus, bipolar electrical energy has a greater local effect on tissue than does monopolar electrical energy.

Based on the foregoing, and assuming the electrode arrangement illustrated in FIG. 6, in method, the DR nerve fibers are rendered less excitable to a subsequent electrical pulse by conveying a sub-threshold, depolarizing, conditioning pre-pulse from left and right electrodes $E_L$, $E_R$ in a monopolar manner, and the DC nerve fibers are subsequently stimulated by conveying a stimulation pulse from the center electrode Ec in a tripolar manner. Notably, although the threshold data of FIGS. 9a-9c were generated based on a rostro-caudal electrode arrangement, the monopolar and tripolar threshold data in particular are expected to have similar trends for the medio-lateral electrode configuration shown in FIG. 6.

Figure 10:
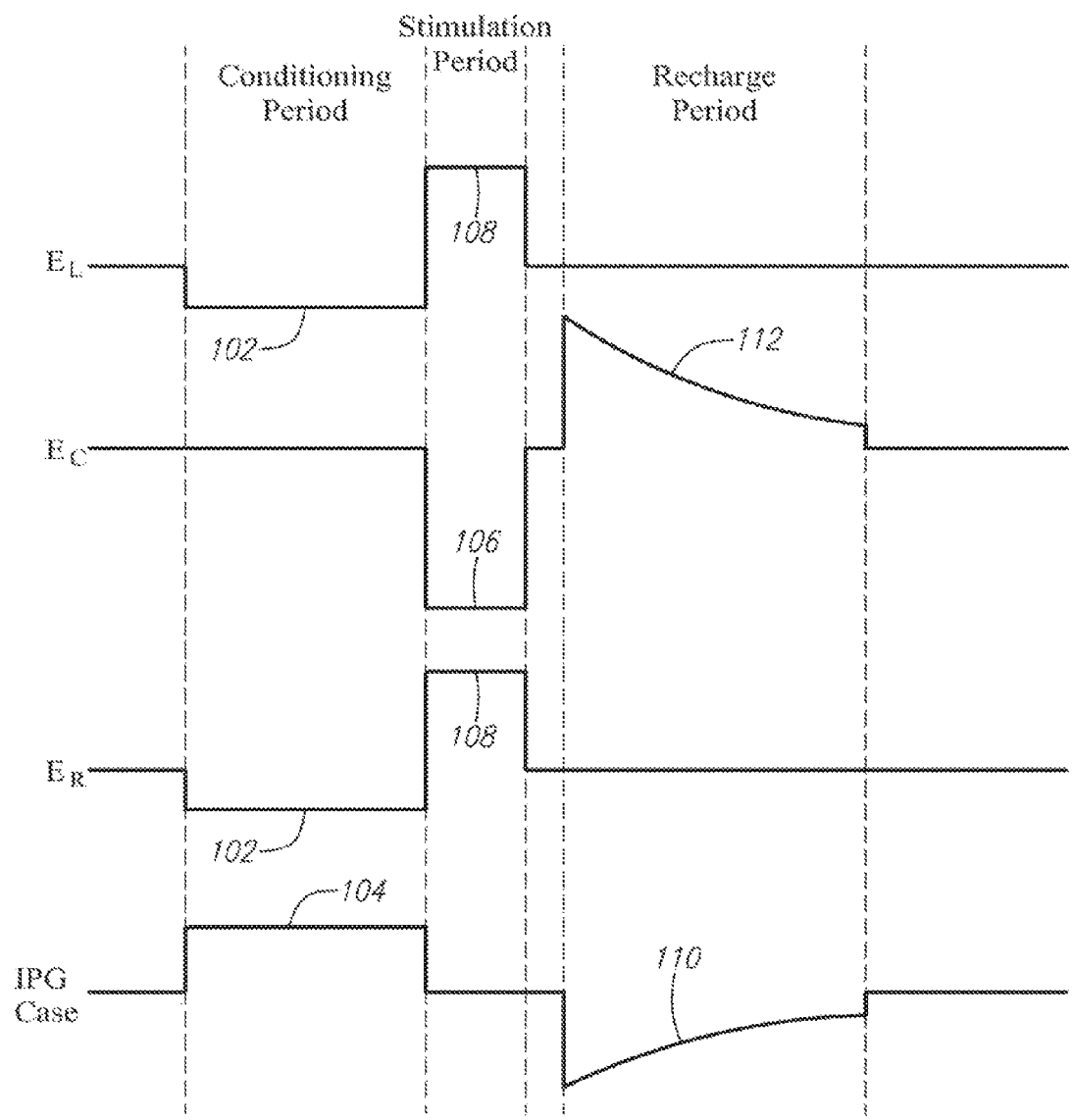
FIG. 10 is one pulse timing diagram used to condition and stimulate the spinal cord with the electrode arrangement of FIG. 6.

In particular, and with further reference to FIG. 10, the IPG 14 outputs depolarizing cathodic conditioning pulses 102 to the left and right electrodes $E_L$, $E_R$ and an anodic pulse 104 to the IPG case in a monopolar manner, during a conditioning period. Because all of the current is conveyed between the left and right electrodes $E_L$, $E_R$ and the IPG case, the sum of the absolute amplitudes of the cathodic conditioning pulses 102 equal the absolute amplitude of the anodic pulse 104, and the widths of the cathodic conditioning pulses 102 and anodic pulse 104 are all equal.

The cathodic conditioning pulses 102 (and thus the anodic pulse 104) have amplitude levels that are relatively low (at a sub-threshold level)(e.g., less than 1 ma) and a pulse width (e.g., greater than 500 µs, and preferably greater than 1 ms) sufficient to condition the DR nerve fibers to be less excitable to subsequent stimulation, with less conditioning or no conditioning of the DC nerve fibers. Notably, because the DR nerve fibers have a lower stimulation threshold relative to the DC nerve fibers with respect to monopolar electrical energy, the cathodic conditioning pulses 102 will provide the desired conditioning effect for the DR nerve fibers while the DC nerve fibers are not expected to be conditioned (i.e., made less excitable) to the same degree prior to subsequent stimulation; that is, the difference between thresholds of the subsequent therapeutic stimulation of the DC nerve fibers and side-effect stimulation of the DR fibers is expected to increase. In addition, because the cathodic conditioning pulses 102 are applied in a monopolar manner, a greater region of tissue is affected, thereby providing broader conditioning of the DR nerve fibers.

The IPG 14 then outputs a cathodic stimulation pulse 106 to the center electrode $E_C$ and anodic pulses 108 to the left and right electrodes $E_L$, $E_R$ in a tripolar manner, during a stimulation period. Because all of the current is conveyed between the center electrode $E_C$ and the left and right electrodes $E_L$, $E_R$, the absolute amplitude of the cathodic stimulation pulse 106 is equal to the sum of the absolute amplitudes of the anodic pulses 108, and the widths of the cathodic stimulation pulse 106 and anodic pulses 108 are all equal.

The cathodic stimulation pulse 106 (and thus, the anodic pulses 108) has an amplitude level that is relatively large (compared to the monopolar conditioning pulse; e.g., 2 ma) and a pulse width (e.g., 200 µs) sufficient to stimulate the DC nerve fibers, yet avoid stimulation of the DR nerve fibers. In the illustrated embodiment, the cathodic stimulation pulse 106 is generated immediately after the cathodic conditioning pulses 102 are generated. That is, there is no time lapse between the conditioning period and the stimulation period. It should be noted that the cathodic stimulation pulse 106 may be generated up to 100 ms after termination of the cathodic conditioning pulses 102.

Significantly, because the DR nerve fibers have been preconditioned to be less excitable to subsequent stimulation, the amplitude level of the cathodic stimulation pulse 106 may be greater than otherwise used if the DR nerve fibers were not preconditioned, thereby allowing greater stimulation of the DC nerve fibers if desired. In addition, because the DC nerve fibers are expected to have a low stimulation threshold relative to the DR nerve fibers with appropriately spaced tripolar stimulation at certain electrode lengths (which may differ from the spacing and electrode lengths for the rostro-caudal electrode configuration shown in FIG. 9a-9c), the DC nerve fibers will preferentially be stimulated over the DR nerve fibers, thereby further alleviating any concern that the DR nerve fibers will be undesirably stimulated. Notably, because the cathodic stimulation pulse 106 is applied in a tripolar manner, stimulation is more localized to the DC nerve fibers.

To avoid electrode degradation and cell trauma, the IPG 14 outputs a cathodic recharge pulse 110 to the IPG case, and an anodic recharge pulse 112 to the center electrode $E_C$, during a recharge period, thereby preventing direct current charge transfer through the tissue. That is, charge is conveyed through the electrode-tissue interface via the anodic current from the IPG case during the conditioning period, and via the cathodic current from the center electrode $E_C$ during the stimulation period, and then pulled back off the electrode-tissue interface via the oppositely polarized cathodic current of the IPG case and the oppositely polarized anodic current of the center electrode $E_C$ during the recharge period.

In the embodiment illustrated in FIG. 10, the recharge pulses 110, 112 are passive in that the electrical energy is provided to the IPG case and center electrode Ec via a recharge or redistribution of the charge flowing from any one or more of the coupling capacitors C1-Cn, while the current sources or voltage sources of the analog output circuitry 50 (shown in FIG. 7) are turned off. Alternatively, the recharge pulses may be active in that the electrical energy is provided to the center electrode $E_C$ and IPG case by turning on the current sources or voltage sources of the analog output circuitry 50 (shown in FIG. 7). Using active recharge in this manner allows faster recharge, while avoiding the charge imbalance that could otherwise occur. Because approximately equally charged cathodic and anodic pulses are applied to the left and right electrodes $E_L$, $E_R$ during the respective conditioning and stimulation periods, separate recharging pulses are not required for these electrodes. In cases where the cathodic and anodic pulses are not charge balanced, the left and right electrodes $E_L$, $E_R$ may also have a passive or active recharge phase, and that phase could be simultaneous with the recharge phase of the IPG case and center electrode $E_C$.

Notably, in some instances, it may be advantageous to preferentially stimulate the DR nerve fibers over the DC nerve fibers. For example, in contrast to DR nerve fiber stimulation, targeting stimulation of DC nerve fibers might not easily achieve paresthesia of a small body part, because the nerves are not well separated in the dorsal column. In addition, the stimulation techniques and electrode arrays used with DC stimulation are not designed to provide resolution of individual nerve rootlet groupings. Moreover, for lower back stimulation, the DC sensor nerve fibers may be embedded deep in the dorsal column, and therefore may be difficult to stimulate. In contrast, nerve rootlets that correspond to a localized body segment, such as a foot, are more easily accessible when stimulating DR nerve fibers.

To this end, the IPG 14 (or ETS 20) may utilize the inherent differences between monopolar electrode arrangements and multipolar electrode arrangements to instead preferentially stimulate DR nerve fibers, while suppressing stimulation of the DC nerve fibers. Using the electrode arrangement illustrated in FIG. 6, the DC nerve fibers are rendered less excitable to a subsequent electrical pulse by conveying a sub-threshold, depolarizing, conditioning pre-pulse from the center electrode $E_C$ in a tripolar manner, and the DR nerve fibers are subsequently stimulated by conveying stimulation pulses from the left and right electrodes $E_L$, $E_R$ in a monopolar manner.

Figure 11:
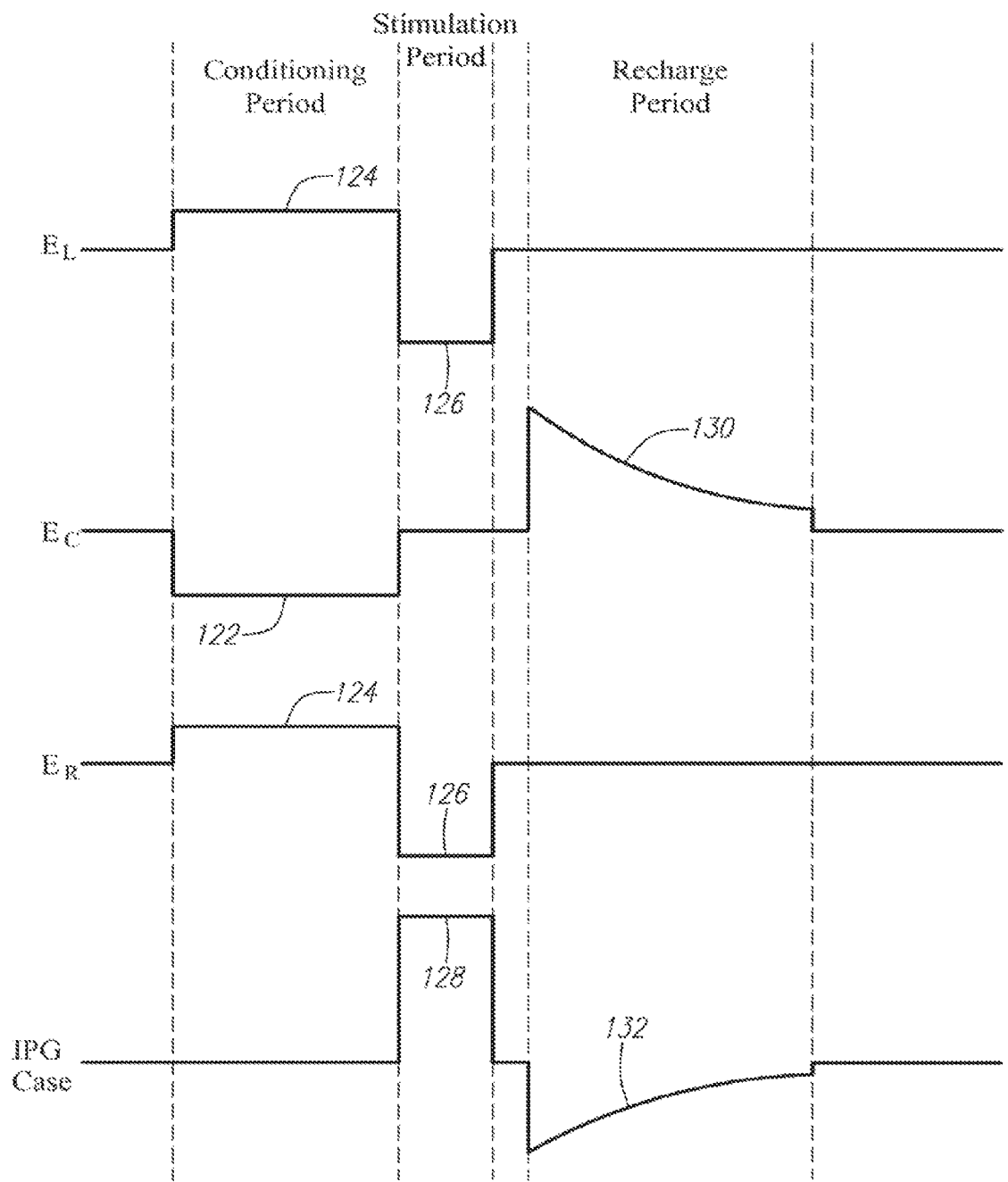
FIG. 11 is another pulse timing diagram used to condition and stimulate the spinal cord with the electrode arrangement of FIG. 6.

In particular, and with further reference to FIG. 11, the IPG 14 outputs a depolarizing cathodic conditioning pulse 122 to the center electrode $E_C$, and anodic pulses 124 to the left and right electrodes $E_L$, $E_R$ in a tripolar manner during a conditioning period. Because all of the current is conveyed between the center electrode $E_C$ and the left and right electrodes $E_L$, $E_R$, the absolute amplitude of the cathodic conditioning pulse 122 is equal to the sum of the absolute amplitudes of the anodic pulses 124, and the width of the cathodic conditioning pulse 122 and anodic pulses 124 are all equal.

In the illustrated embodiment, the cathodic conditioning pulse 122 (and thus the anodic pulses 124) has an amplitude level (at a sub-threshold level)(e.g., less than 1 ma) and a pulse width (e.g., greater than 500 µs, and preferably greater than 1 ms) sufficient to condition the DC nerve fibers to be less excitable to subsequent stimulation, without conditioning the DR nerve fibers to the same degree. Notably, because the field decay for a multipolar conditioning pulse is rapid as compared to the field decay for a monopolar conditioning pulse, the amplitude of the cathodic conditioning pulse may be greater than 1 ma. Significantly, because the DC nerve fibers have a lower stimulation threshold relative to the DR nerve fibers with respect to tripolar electrical energy, the cathodic conditioning pulse 122 will provide the desired conditioning effect for the DC nerve fibers, and the DR nerve fibers will not be conditioned (i.e., made less excitable) to the same degree for subsequent stimulation; that is, subsequent therapeutic stimulation of the DR nerve fibers will not be suppressed to the degree that DC fibers are suppressed, such that the therapeutic stimulation of the DR fibers is still enabled.

The IPG 14 then outputs cathodic stimulation pulses 126 to the left and right electrodes $E_L$, $E_R$ and an anodic pulse 126 to the IPG case during a stimulation period. Because all of the current is conveyed between the left and right electrodes $E_L$, $E_R$ and the IPG case, the sum of the absolute amplitudes of the cathodic stimulation pulses 126 equal the absolute amplitude of the anodic pulse 128, and the widths of the cathodic stimulation pulses 126 and cathodic pulse 128 are all equal.

In the illustrated embodiment, the cathodic stimulation pulses 126 (and thus, the anodic pulse 128) have amplitude levels (e.g., 2 ma) and a pulse width (e.g., 200 µs) sufficient stimulate the DR nerve fibers, yet avoid stimulation of the DC nerve fibers. Notably, because the field decay for a monopolar stimulation pulse is slow compared to the field decay for a multipolar stimulation pulse, the amplitude level for the cathodic stimulation pulses 126 may be greater than 2 ma. Significantly, because the DC nerve fibers have been preconditioned to be less excitable to subsequent stimulation, the amplitude levels of the cathodic stimulation pulses 126 may be greater than otherwise used if the DC nerve fibers were not preconditioned, thereby allowing greater stimulation of the DR nerve fibers if desired. In addition, because the DR nerve fibers have a low stimulation threshold relative to the DC nerve fibers with respect to monopolar stimulation, the DR nerve fibers will preferentially be stimulated over the DC nerve fibers, thereby further alleviating any concern that the DC nerve fibers will be undesirably stimulated.

To avoid electrode degradation and cell trauma, the IPG 14 outputs a cathodic recharge pulse 130 to the center electrode $E_C$, and an anodic recharge pulse 132 to the IPG case, during a recharge period, thereby preventing direct current charge transfer through the tissue. That is, charge is conveyed through the electrode-tissue interface via the anodic current from the center electrode $E_C$ during the conditioning period, and via the cathodic current from the IPG case during the stimulation period, and then pulled back off the electrode-tissue interface via the oppositely polarized cathodic current of the center electrode $E_C$ and the oppositely polarized anodic current of the IPG case during the recharge period. As previously described with respect to the recharge pulses 110, 112, the recharge pulses 130, 132 are illustrated as being passive, although they may be active as well. Again, because approximately equally charged anodic and cathodic pulses are applied to the left and right electrodes $E_L$, $E_R$ during the respective conditioning and stimulation periods, separate recharging pulses are not required for these electrodes. In cases where the cathodic and anodic pulses are not charge balanced, the left and right electrodes $E_L$, $E_R$ may also have a passive or active recharge phase, and that phase could be simultaneous with the recharge phase of the IPG case and center electrode $E_C$.

While the above-described embodiments have been described as generating depolarizing monopolar conditioning pulses to suppress the excitability of non-target tissue, and in this case, the DR nerve fibers or DC nerve fibers, hyperpolarizing monopolar or multipolar conditioning pulses can be used to increase the excitability of target tissue. For example, if the DR nerve fibers are the target tissue to be stimulated, they can be rendered more excitable to a subsequent electrical pulse by conveying a sub-threshold, hyperpolarizing, conditioning pre-pulse from the left and right electrodes $E_L$, $E_R$ in a monopolar manner, and then stimulated by conveying stimulation pulses from the left and right electrodes $E_L$, $E_R$ in a multipolar manner.

Figure 12:
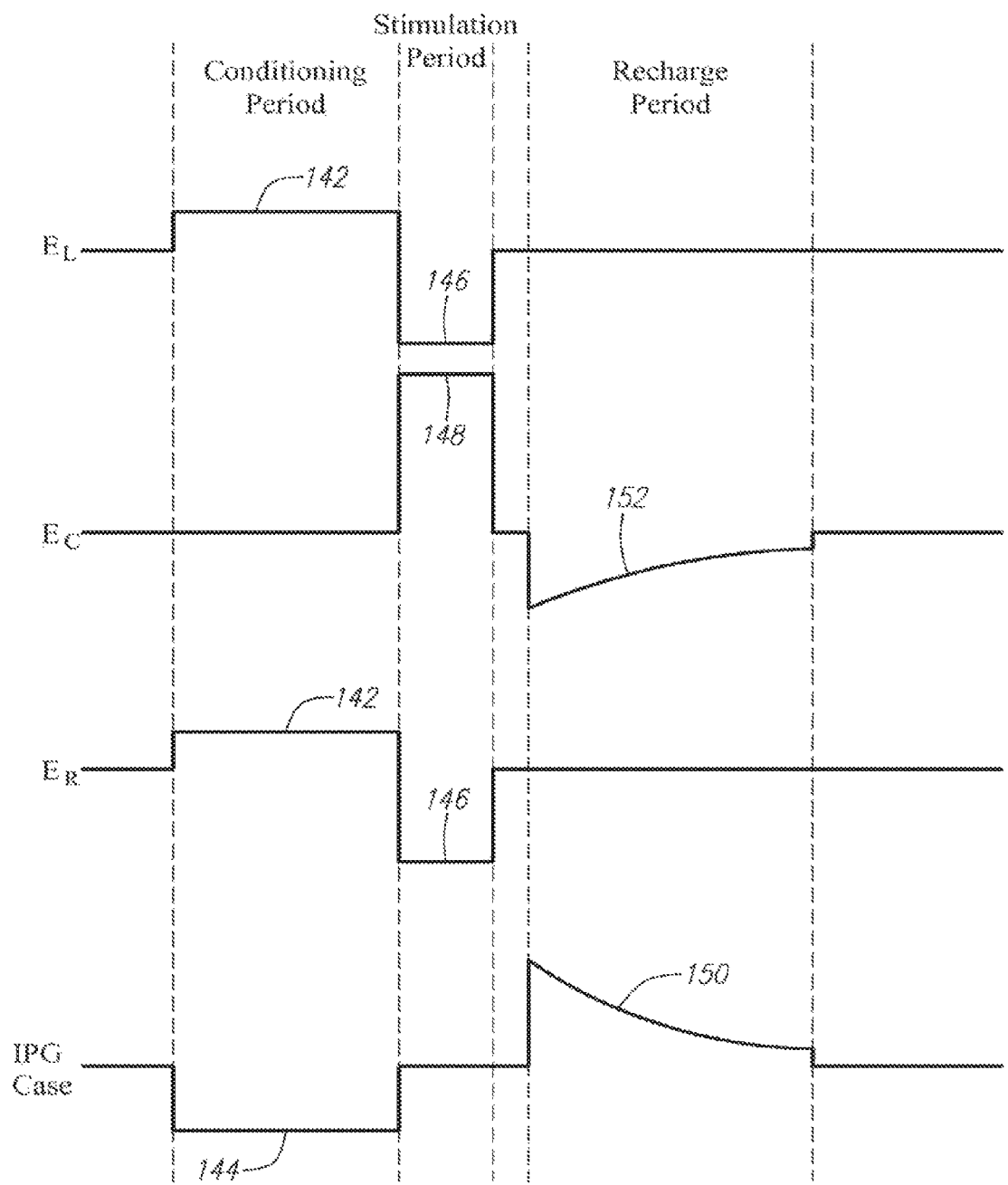
FIG. 12 is still another pulse timing diagram used to condition and stimulate the spinal cord with the electrode arrangement of FIG. 6.

In particular, and with further reference to FIG. 12, the IPG 14 outputs hyperpolarizing anodic conditioning pulses 142 to the left and right electrodes $E_L$, $E_R$ and a cathodic pulse 144 to the IPG case in a monopolar manner, during a conditioning period. Because all of the current is conveyed between the left and right electrodes $E_L$, $E_R$ and the IPG case, the sum of the absolute amplitudes of the anodic conditioning pulses 142 equal the absolute amplitude of the cathodic pulse 144, and the widths of the anodic conditioning pulses 142 and cathodic pulse 144 are all equal.

The anodic conditioning pulses 142 (and thus the cathodic pulse 144) have amplitude levels that are relatively low (at a sub-threshold level)(e.g., less than 1 ma) and a pulse width (e.g., greater than 500 µs, and preferably greater than 1 ms) sufficient to condition the DR nerve fibers to be more excitable to subsequent stimulation, without conditioning the DC nerve fibers. Notably, because the DR nerve fibers have a lower stimulation threshold relative to the DC nerve fibers with respect to monopolar electrical energy, the anodic conditioning pulses 142 will provide the desired conditioning effect preferentially for the DR nerve fibers while the DC nerve fibers are not expected to be conditioned (i.e., made more excitable) to the same degree prior to subsequent stimulation; that is, the difference between thresholds of the subsequent therapeutic stimulation of the DR nerve fibers and side-effect stimulation of the DC fibers is expected to increase. In addition, because the anodic conditioning pulses 142 are applied in a monopolar manner, a greater region of tissue is affected, thereby providing broader conditioning of the DR nerve fibers.

The IPG 14 then outputs cathodic stimulation pulses 146 to the left and right electrodes $E_L$, $E_R$, and an anodic pulse 148 to the center electrode $E_C$ in a tripolar manner, during a stimulation period. Because all of the current is conveyed between the left and right electrodes $E_L$, $E_R$ and the center electrode $E_C$, the sum of the absolute amplitudes of the cathodic stimulation pulses 146 is equal to the absolute amplitude of the anodic pulse 148, and the widths of the cathodic stimulation pulses 146 and anodic pulse 108 are all equal.

The cathodic stimulation pulses 146 (and thus, the anodic pulse 148) have amplitude levels that are relatively large (e.g., 2 ma) and a pulse width (e.g., 200 µs) sufficient to stimulate the DR nerve fibers, yet avoid stimulation of the DC nerve fibers. In the illustrated embodiment, the cathodic stimulation pulses 146 are generated immediately after the anodic conditioning pulses 142 are generated. That is, there is no time lapse between the conditioning period and the stimulation period. It should be noted that the cathodic stimulation pulses 146 may be generated up to 100 ms after termination of the anodic conditioning pulses 142.

Significantly, because the DR nerve fibers have been preconditioned to be more excitable to subsequent stimulation, the amplitude level of the cathodic stimulation pulse 106 may be less than otherwise used if the DR nerve fibers were not preconditioned, thereby allowing greater stimulation of the DR nerve fibers if desired. In addition, because the DR nerve fibers have a low stimulation threshold relative to the DC nerve fibers at certain electrode spacings and lengths (which may differ from the electrode spacing and lengths for the rostro-caudal electrode configuration shown in FIG. 9*a*-9*c*), the DR nerve fibers will preferentially be stimulated over the DC nerve fibers, thereby further alleviating any concern that the DC nerve fibers will be undesirably stimulated. Notably, because the cathodic stimulation pulses 146 are applied in a tripolar manner, stimulation is more localized to the DR nerve fibers.

To avoid electrode degradation and cell trauma, the IPG 14 outputs an anodic recharge pulse 150 to the IPG case, and a cathodic recharge pulse 152 to the center electrode $E_C$, during a recharge period, thereby preventing direct current charge transfer through the tissue. That is, charge is conveyed through the electrode-tissue interface via the cathodic current from the IPG case during the conditioning period, and via the anodic current from the center electrode $E_C$ during the stimulation period, and then pulled back off the electrode-tissue interface via the oppositely polarized anodic current of the IPG case and the oppositely polarized cathodic current of the center electrode Ec during the recharge period. As previously described with respect to the recharge pulses 110, 112, the recharge pulses 150, 152 are illustrated as being passive, although they may be active as well. Again, because approximately equally charged anodic and cathodic pulses are applied to the left and right electrodes $E_L$, $E_R$ during the respective conditioning and stimulation periods, separate recharging pulses are not required for these electrodes. In cases where the cathodic and anodic pulses are not charge balanced, the left and right electrodes $E_L$, $E_R$ may also have a passive or active recharge phase, and that phase could be simultaneous with the recharge phase of the IPG case and center electrode $E_C$.

Notably, although foregoing monopolar/tripolar conditioning/stimulation techniques have been described in the context of a medio-lateral electrode configuration in order to take advantage of spatial proximity of the contacts to the fibers (i.e., the left and right electrodes $E_L$, $E_R$ will preferentially act on the DR nerve fibers due to their spatial proximity to the DR nerve fibers, and the center electrode $E_C$ will preferentially act on the DC nerve fibers due to its spatial proximity to the midline of the spinal cord SC), similar techniques can be performed using a rostral-caudal electrode configuration, which is predominantly the electrode configuration used today, to take advantage of the spaced longitudinal field created by the longitudinally arranged electrodes when operated in a multipolar manner, thereby preferentially acting on the DC fiber nerves.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of providing therapy to a patient using a pulse generator that includes pulse generation circuitry and using electrodes electrically connected to the pulse generation circuitry, the method comprising:
   delivering at least one conditioning pulse pattern using the pulse generation circuitry of the pulse generator in one of a monopolar manner using one of the electrodes or in a multipolar manner using at least two of the electrodes, wherein the at least one conditioning pulse pattern includes at least one subthreshold pulse pattern to change tissue excitability to subsequent stimulation; and
   delivering at least one stimulation pulse pattern using the pulse generation circuitry of the pulse generator in the other one of the monopolar manner using one of the electrodes or the multipolar manner using at least two of the electrodes,
   wherein either:
      the at least one conditioning pulse pattern is delivered in a monopolar manner using one of the electrodes and the at least one stimulation pulse pattern is delivered in a multipolar manner using at least two of the electrodes; or
      the at least one conditioning pulse pattern is delivered in a multipolar manner using at least two of the electrodes and the at least one stimulation pulse pattern is delivered in a monopolar manner using one of the electrodes;
   wherein the at least one conditioning pulse pattern is either:
      at least one depolarizing pulse pattern delivered from the plurality of electrodes to render a first region of the tissue less excitable to stimulation, and the at least one stimulation pulse pattern is delivered from the plurality of electrodes to stimulate a second different region of the tissue; or
      at least one hyperpolarizing pulse pattern delivered from the plurality of electrodes to render the first region of the tissue more excitable to stimulation, and the at least one stimulation pulse pattern is delivered from the plurality of electrodes to stimulate the first tissue region.

2. The method of claim 1, wherein the at least one conditioning pulse pattern is the at least one depolarizing pulse pattern to render the first region of the tissue less excitable to stimulation, and the at least one stimulation pulse pattern is to stimulate the second different region of the tissue.

3. The method of claim 2, wherein the first tissue region is one or more dorsal root nerve fibers, and the second tissue region is one or more dorsal column nerve fibers.

4. The method of claim 2, wherein the first tissue region is one or more dorsal column nerve fibers, and the second tissue region is one or more dorsal root nerve fibers.

5. The method of claim 1, wherein the at least one conditioning pulse pattern is the at least one hyperpolarizing pulse pattern to render the first region of the tissue more excitable to stimulation, and the at least one stimulation pulse pattern is to stimulate the first tissue region.

6. The method of claim 5, wherein the first tissue region is one or more dorsal column nerve fibers.

7. The method of claim 1, wherein the at least one conditioning pulse pattern is delivered in a monopolar manner, and the at least one stimulation pulse pattern is delivered in a multipolar manner.

8. The method of claim 1, wherein the at least one conditioning pulse pattern is delivered before the at least one stimulation pulse pattern is delivered.

9. A method of providing therapy to a patient using a pulse generator that includes pulse generation circuitry and using a plurality of electrodes electrically connected to the pulse generation circuitry, the method comprising:
    delivering at least one conditioning pulse pattern using the pulse generation circuitry of the pulse generator from the plurality of electrodes in contact with tissue of a patient in one of a monopolar manner and a multipolar manner, wherein the at least one conditioning pulse pattern includes at least one subthreshold pulse to change tissue excitability to subsequent stimulation; and
    delivering at least one stimulation pulse pattern using the pulse generation circuitry of the pulse generator from the plurality of electrodes in a different one of the monopolar manner and the multipolar manner,
    wherein the at least one conditioning pulse pattern is delivered from the plurality of electrodes in a multipolar manner, and the at least one stimulation pulse is delivered from the plurality of electrodes in a monopolar manner.

10. The method of claim 9, wherein the at least one conditioning pulse pattern is at least one depolarizing pulse pattern delivered from the plurality of electrodes to render one or more dorsal root nerve fibers less excitable to stimulation, and the at least one stimulation pulse pattern is delivered from the plurality of electrodes to stimulate one or more dorsal column nerve fibers.

11. The method of claim 9, wherein the at least one conditioning pulse pattern is at least one depolarizing pulse pattern delivered from the plurality of electrodes to render one or more dorsal column nerve fibers less excitable to stimulation, and the at least one stimulation pulse pattern is delivered from the plurality of electrodes to stimulate one or more dorsal root nerve fibers.

12. The method of claim 9, wherein the at least one conditioning pulse pattern is at least one hyperpolarizing pulse pattern delivered from the plurality of electrodes to render one or more dorsal column nerve fibers more excitable to stimulation, and the at least one stimulation pulse pattern is delivered from the plurality of electrodes to stimulate the one or more dorsal column nerve fibers.

13. The method of claim 9, wherein the at least one conditioning pulse pattern is delivered from the plurality of electrodes before the at least one stimulation pulse pattern is delivered from the plurality of electrodes.

14. The method of claim 9, wherein the tissue is a spinal cord, and the plurality of electrodes are transversely arranged relative to the axis of the spinal cord.

15. A method of providing therapy to a patient using a pulse generator that includes pulse generation circuitry and using electrodes electrically connected to the pulse generation circuitry and transversely arranged relative to an axis of a spinal cord for a patient, the method comprising:
    delivering at least one conditioning pulse pattern using the pulse generation circuitry of the pulse generator in one of a monopolar manner using one of the electrodes or in a multipolar manner using at least two of the electrodes, wherein the at least one conditioning pulse pattern includes at least one subthreshold pulse pattern to change tissue excitability to subsequent stimulation; and
    delivering at least one stimulation pulse pattern using the pulse generation circuitry of the pulse generator from the plurality of electrodes in a different one of the monopolar manner and the multipolar manner.

16. The method of claim 15, wherein the at least one conditioning pulse pattern is at least one depolarizing pulse pattern conveyed from the plurality of electrodes to render one or more dorsal root nerve fibers less excitable to stimulation, and the at least one stimulation pulse pattern is delivered from the plurality of electrodes to stimulate one or more dorsal column nerve fibers.

17. The method of claim 15, wherein the at least one conditioning pulse pattern is at least one depolarizing pulse pattern conveyed from the plurality of electrodes to render one or more dorsal column nerve fibers less excitable to stimulation, and the at least one stimulation pulse pattern is delivered from the plurality of electrodes to stimulate one or more dorsal root nerve fibers.

18. The method of claim 15, wherein the at least one conditioning pulse is at least one hyperpolarizing pulse pattern conveyed from the plurality of electrodes to render one or more dorsal column nerve fibers more excitable to stimulation, and the at least one stimulation pulse pattern is delivered from the plurality of electrodes to stimulate the one or more dorsal column nerve fibers.

19. The method of claim 15, wherein the at least one conditioning pulse pattern is delivered from the plurality of electrodes before the at least one stimulation pulse pattern is delivered from the plurality of electrodes.

20. The method of claim 15, wherein the at least one conditioning pulse pattern is delivered from the plurality of electrodes in a multipolar manner, and the at least one stimulation pulse pattern is delivered from the plurality of electrodes in a monopolar manner.

* * * * *